United States Patent [19]

Schneider et al.

[11] 4,139,714

[45] * Feb. 13, 1979

[54] CATALYTIC CODIMERIZATION OF NORBORNADIENE WITH AN ACRYLIC ACID ESTER

[75] Inventors: Abraham Schneider, Overbrook Hills; Harry K. Myers, Jr., Aston, both of Pa.

[73] Assignee: Sun Oil Company of Pennsylvania, Philadelphia, Pa.

[*] Notice: The portion of the term of this patent subsequent to Aug. 15, 1995, has been disclaimed.

[21] Appl. No.: 812,206

[22] Filed: Jul. 1, 1977

[51] Int. Cl.$^2$ ............................................. C07C 69/74
[52] U.S. Cl. ..................... 560/116; 562/198; 260/666 PY
[58] Field of Search ......................................... 560/116

[56] References Cited

U.S. PATENT DOCUMENTS

| | | | |
|---|---|---|---|
| 2,940,984 | 6/1960 | Applequist et al. | 560/116 |
| 3,271,438 | 9/1966 | Cannell | 560/116 |
| 3,641,175 | 2/1972 | Wilke et al. | 260/666 B |

OTHER PUBLICATIONS

Noyori et al., JACS 97:4, pp. 812–820, (1975).

*Primary Examiner*—Jane S. Myers
*Attorney, Agent, or Firm*—J. Edward Hess; Donald R. Johnson; Anthony Potts, Jr.

[57] ABSTRACT

Norbornadiene and an acrylic acid ester, e.g. methyl acrylate, are catalytically codimerized in the presence of a three-component homogeneous catalytic system consisting of nickel acetylacetonate, an alkyl aluminum chloride and triphenylphosphine. The resulting codimer can be used as a precursor for missile fuel. The ester portion of the acrylic acid ester is the radical RCH$_2$O- wherein the R is an H or an alkyl containing up to 10 carbon atoms.

11 Claims, No Drawings

CATALYTIC CODIMERIZATION OF NORBORNADIENE WITH AN ACRYLIC ACID ESTER

The invention herein described was made in the course of or under a contract thereunder with the United States Air Force Systems Command.

CROSS REFERENCE TO RELATED APPLICATIONS

This application is related to applicant's U.S. Patent Ser. No. 812,207 and 812,209, filed the same date.

BACKGROUND OF THE INVENTION

The invention relates to the catalytic codimerization of norbornadiene, hereinafter referred to as NBD, and acrylic acid ester, hereinafter referred to as AAE. Particularly the invention relates to the preparation of a codimer using a specified catalyst system.

Resulting codimer can be used as a precursor for a missile fuel. The codimer can be hydrolyzed to an acid which can be decarboxylated. The resulting decarboxylated hydrocarbon can be used as a missile fuel.

NBD is also known as bicyclo-(2.2.1) heptadiene-2,5. A method of preparation is disclosed in U.S. Pat. No. 2,875,256 issued Feb. 24, 1959. The NBD can be represented by either one of the following structural formulas:

 OR 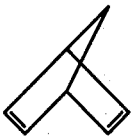

(I)         (I)

NBD can be easily dimerized to an exo-exo hexacyclic dimer. Thus one problem in reacting NBD with another hydrocarbon reactant is to minimize the formation of the foregoing dimer while encouraging the formation of the desired codimer.

In the Journal of the American Chemical Society /97:4/ Feb. 19, 1975, pages 812 & ff., R. Noyori et al in an article titled "Nickel (0)-Catalyzed Reaction of Quadricyclane with Electron-Deficient Olefins" discloses the reaction of alkyl acrylate and NBD using bis(acrylonitrile) nickel (0). With methyl acrylate the resulting product has the following structure:

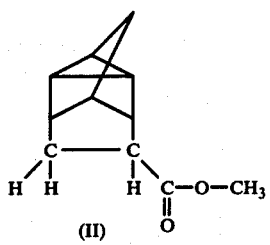

(II)

The reaction was run at various temperatures for a substantial amount of time. Yet, the yield of codimer II was very low.

Thus as the aforementioned article indicates the specific synthesis problem is to obtain codimer II and related codimers in both a high conversion and selectivity and with a rapid reaction rate.

SUMMARY OF THE INVENTION

Rapid codimerization of NBD and AAE is obtained using a catalytic amount of a three component homogeneous catalytic system consisting of nickel acetylacetonate, one of three alkyl aluminum chlorides and triphenyl phosphine. Both the yield and selectivity as to codimer II (which structure is described hereinafter) are improved and the reaction rate is relatively rapid. Resulting codimer can be a precursor to a missile fuel.

DESCRIPTION OF THE INVENTION

The catalytic codimerization of NBD and AAE via present invention can be represented by the following formula reaction:

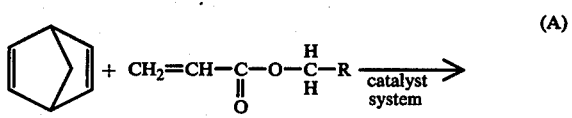

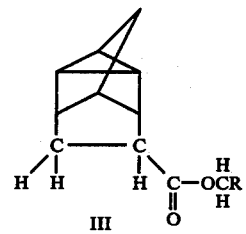

III (A)

wherein R is an H or an alkyl containing up to 10 carbon atoms. The alkyl can be ethyl, propyl, butyl, and, up to and including decyl. As shown NBD and AAE are contacted in the presence of a catalytic amount of the catalyst system defined herein.

The NBD used can contain a nominal amount of similar hydrocarbons, however, which if present should not be a type which could adversely effect the reaction. If the NBD used contains such an undesirable hydrocarbon it can be removed by known means. The foregoing also applies to the AAE used. Thus the materials used in the invention can consist essentially of NBD and AAE.

In the codimerization of NBD and AAE one mole of each reacts with the other to form one mole of the NBD-AAE codimer III. However, if the NBD to AAE mole ratio is too large NBD homodimerization can occur with its adverse effect on yields. On the other hand if the NBD to AAE mole ratio is too low then the yield per pass can be too low and hence uneconomical. Within the aforementioned limits a preferred NBD to AAE mole ratio is in the range between from about 0.1 to about 20 with about 0.2 to about 5 more preferred.

The catalytic system favoring the aformentioned codimerization reaction (A) contains three components. The three are nickel acetylacetonate, hereinafter referred to as NiA$_2$, triphenyl phosphine, hereinafter referred to as TPP, and an alkyl aluminum chloride selected from the group consisting of diethylaluminum chloride, ethyl aluminum dichloride and ethyl aluminum sesquichloride. The latter three are hereinafter referred to as DEAC, EADC and EASC respectively. The NiA$_2$ can be the hydrate (2H$_2$O) or anhydrous form. The amount of system present is a catalytic amount so that a suitable conversion to codimer III occurs and the selectivity as to it is sufficient. Material, which during the codimerization reaction could adversely affect the catalyst system, should not be present.

For example, the presence of hydroxylic compounds such as water, alcohol or oxygen from air could deactivate the catalyst system. All three components of the catalyst system are commercially available and methods for their preparation are reported in the literature.

The amount of NBD present compared to the $NiA_2$ should be catalytically sufficient to obtain the desired product. Generally the NBD to $NiA_2$ mole ratio can range between from about 10 to about 2000 with a preferred range between from about 20 to about 500.

DEAC, EADC or EASC is the second component of the catalyst system with DEAC preferred. The amount of this component can vary substantially but generally it relates to the amount of $NiA_2$ used. An effective DEAC, EADC or EASC to $NiA_2$ mole ratio can be between from about 1 to about 100 with from about 3 to about 50 preferred and from about 5 to about 20 more preferred. Excess DEAC, EADC or EASC also serves as a scavenger. Generally, however, when DEAC, EADC or EASC is used it is advantageous to conduct the reaction under substantially anhydrous conditions and under an inert gas blanket.

The third component of the catalyst system is TPP which has the formula $(C_6H_5)_3P$. The amount of this component of the catalyst system should be catalytically sufficient to obtain the desired product, however, generally the amount present is related to the amount of $NiA_2$ present. Generally the TPP to $NiA_2$ mole ratio can range between from about 0.1 to about 100 with a preferred range between from about 0.25 to about 20.

Selectivity refers to the amount of a particular compound formed divided by the amount of all compounds formed. From a commercial standpoint economics of an overall process determines the optimal levels for both the selectivity and yield.

The reaction time required for an economically satisfactory selectivity and/or yield depends on a number of factors, such as catalyst to feed ratio, as well as operating conditions. Also the economics depend on capital investment versus conversion per pass and the like. Catalyst to feed ratios are discussed herein while typical conditions are provided by the Example.

A solvent can be used in the codimerization reaction. The solvent can be inert or it can be the NBD itself. Since the reaction is mildly exothermic the solvent can serve as a heat sink. It can also assist in solubilizing the reaction components, that is the feed and the components of the catalyst, and thereby provide for a homogeneous reaction medium. Some solvent can be added to the system as a carrier for one or more of the catalyst components. For example, DEAC is often maintained in a solvent such as toluene. Furthermore, the solvent should not adversely react with the feed, products or catalyst, therefore, if it is not NBD, it should be inert. Also, presence of the solvent can facilitate the handling of the reaction mixture. Classes of suitable inert solvents include aromatic hydrocarbons, cycloparaffins, cycloolefins, ethers, halogenated aromatics, halogenated paraffins and halogenated cycloparaffins. Specific examples include benzene, toluene, xylenes, cyclohexane, cyclopentene, diethylether, chlorobenzene, bromobenzene, chlorinated cyclohexane and the like. As to the amount of solvent used, excessive amounts decrease the reaction rate, and thus adversely effect the economics for a commercial operation.

The codimerization of NBD and AAE with the three component catalyst system can occur at ambient temperature. Thus the temperature of the homogeneous feed catalyst system mixture need not be raised to initiate reaction A. Of course, if the mixture is at an extremely low temperature, then heating of the cooled mixture could be necessary. However, once reaction A is underway, some heat is generated and the temperature of the mixture increases. If the temperature increases too much then some cooling would be required. Generally, however, the codimerization of NBD and AAE with a reasonable amount of the three-component catalyst system is not characterized by an extremely rapid exotherm.

Selective codimerization of the NBD and AAE occurs in a liquid phase therefore it is not desirable to have the reaction temperature largely exceed the boiling points of the NBD and/or any solvent. Conversely, if the temperature is too low the reaction rate would be too low to be economically feasible. An operable temperature range is between from about $-20°$ C. to about $100°$ C. with about $25°$ C. to about $85°$ C. a preferred range. The operating pressure can vary substantially, however, it can range from about atmospheric up to about 2000 psi with 1000 psi a preferred upper value. Process economics favor lower operating pressure.

To further illustrate the invention the following examples are provided:

EXAMPLES

The accompanying Table summarizes the codimerization runs. Run 1 indicates that at the conditions shown the selectivity as to the codimer II is high at a relatively low NBD/MA volume ratio. Run 2 suggests that at a relatively higher NBD/MA volume ratio the selectivity as to the codimer II may decline.

In runs 1-2 the $NiA_2$ hydrate, the phosphine, solvent (benzene), NBD, and the methyl acrylate were added to a Fisher-Porter reaction vessel at a temperature of about $24°$ C. The materials were mixed together and deaerated with argon and then warmed to $60°-70°$ C. to dissolve the nickel compound. Afterward the mixture was cooled to a temperature of about $20°$ C. At the low temperature the DEAC was added and the mixture warmed. The maximum temperature obtained during the run is shown in the Table along with the time. Yields and selectivities were determined by vapor phase chromatographic analysis.

Analogous results will be obtained when other acrylic acid esters such as ethyl, propyl, butyl and decyl acrylate are used in lieu of the aforementioned methyl acrylate when using the NiA-alkyl aluminum chloride-phosphine catalyst system. Also analogous results will be obtained when the DEAC is replaced by EADC or EASC or the $NiA_2$ hydrate is replaced by its anhydrous form.

The yields are based on the amount of codimer present in the resulting reaction mixture which contains unreacted reactants and solvent.

TABLE

CONDITIONS FOR CODIMERIZATION OF NBD & METHYL ACRYLATE (MA)

| Run[1] | Metal[2] | Volume Ratio of NBD/MA[3] | Phosphine & Amount (mg) | Weight Ratio of NiA/Phosphine | Temp. °C Max. | Hrs. | Yield % | Selectivity % Codimer | Penta-Cyclics | Hexa-Cyclics | Binor-S |
|---|---|---|---|---|---|---|---|---|---|---|---|
| 1 | NiA$_2$ | 2.5 | TPP (10) | 0.7 | 70 | 4.8 | <5 | 98 | — | 2 | — |
| 2 | NiA$_2$ | 10 | TPP (19) | 0.4 | 80 | 15 | <5 | 32 | 67 | 1 | — |

[1] The alkyl aluminum chloride used is DEAC
[2] NiA$_2$ is the hydrate
[3] The amount of NBD used was 9.8 millimoles.

The invention claimed is:

1. Process for the catalytic codimerization of norbornadiene with an acrylic acid ester comprising:
   (a) contacting norbornadiene and an acrylic acid ester, wherein the ester portion is RCH$_2$O— and R is an H or an alkyl containing one to ten carbon atoms, in the presence of a catalytic amount of a three-component homogeneous catalytic system consisting of nickel acetylacetonate, triphenylphosphine, and an alkyl aluminum chloride selected from the group consisting of diethylaluminum chloride, ethyl aluminum dichloride, ethyl aluminum sesquichloride;
   (b) having the contacting occurring at a temperature within the range between from about −20° C. to about 100° C.; and
   (c) continuing the contacting until a norbornadiene - acrylic acid ester codimer having the following structure

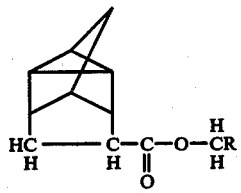

is prepared.

2. Process according to claim 1 wherein the norbornadiene to the ester mole ratio is in the range between from about 0.1 to about 20.

3. Process according to claim 1 wherein the triphenylphosphine to the acetylacetonate mole ratio is in the range between from about 0.1 to about 100.

4. Process according to claim 1 wherein the norbornadiene to the acetylacetonate mole ratio is in the range between from about 10 to about 2000.

5. Process according to claim 1 wherein the alkyl aluminum chloride to the acetylacetonate mole ratio is in the range between from about 1 to about 100.

6. Process according to claim 4 wherein an inert solvent is present.

7. Process according to claim 6 wherein the solvent is selected from the group consisting of aromatic hydrocarbon, cycloparaffin, cycloolefin, ether, halogenated aromatic halogenated paraffin and halogenated cycloparaffin.

8. Process according to claim 7 wherein the norbornadiene to the ester mole ratio is in the range between from about 0.1 to about 20.

9. Process according to claim 8 wherein the triphenylphosphine to the acetylacetonate mole ratio is in the range between from about 0.1 to about 100.

10. Process according to claim 9 wherein the norbornadiene to the acetylacetonate mole ratio is in the range between from about 10 to about 2000.

11. Process according to claim 10 wherein the ester is methyl acrylate.